United States Patent [19]

Meador

[11] 4,046,148

[45] Sept. 6, 1977

[54] SEVERING AND CAUTERIZING INSTRUMENT FOR USE IN SEVERING TAILS AND NAVEL CORDS

[76] Inventor: Lawrence Dean Meador, R.R. 2, Lanark, Ill. 61046

[21] Appl. No.: 761,771

[22] Filed: Jan. 24, 1977

Related U.S. Application Data

[63] Continuation of Ser. No. 565,448, April 7, 1975, abandoned.

[51] Int. Cl.² ............... A61B 17/32; A61B 17/36
[52] U.S. Cl. ............... 128/303.1; 30/140; 219/227; 219/230; 219/533; 128/305
[58] Field of Search ............ 30/140; 81/9.5 R, 9.5 A; 128/303.1, 303.14, 303.17, 305; 219/221, 227, 230, 533

[56] References Cited

U.S. PATENT DOCUMENTS

| 365,179 | 6/1887 | Hale | 81/9.5 R UX |
|---|---|---|---|
| 1,083,386 | 1/1914 | Chapman | 128/303.1 X |
| 1,456,639 | 5/1923 | Lagier | 128/303.1 |
| 1,763,894 | 6/1930 | Lagier | 128/303.1 |
| 2,032,688 | 3/1936 | Dart | 30/140 |
| 2,674,796 | 4/1954 | Herold | 81/9.5 R X |
| 2,780,713 | 2/1957 | Helbling | 128/303.1 |
| 3,117,578 | 1/1964 | Helbling | 128/303.14 |
| 3,980,861 | 9/1976 | Fukunaga | 219/230 |

FOREIGN PATENT DOCUMENTS 2,301,417  8/1973  Germany ............... 81/9.5 R

Primary Examiner—Channing L. Pace
Attorney, Agent, or Firm—Leydig, Voit, Osann, Mayer & Holt, Ltd.

[57] ABSTRACT

The instrument includes a first handle and a first blade pivotally connected scissors-fashion with a second handle and a second blade. One of the blades is formed with a first notch for severing the tail of a pig and with a second notch for severing the navel cord of the pig. A heating unit heats the other blade in order to cauterize the tail or navel cord as an incident to the severing operation. The heating unit includes a handle which coacts with the other two handles to define a tripod for supporting the instrument in a standing position when the instrument is not in use.

5 Claims, 4 Drawing Figures

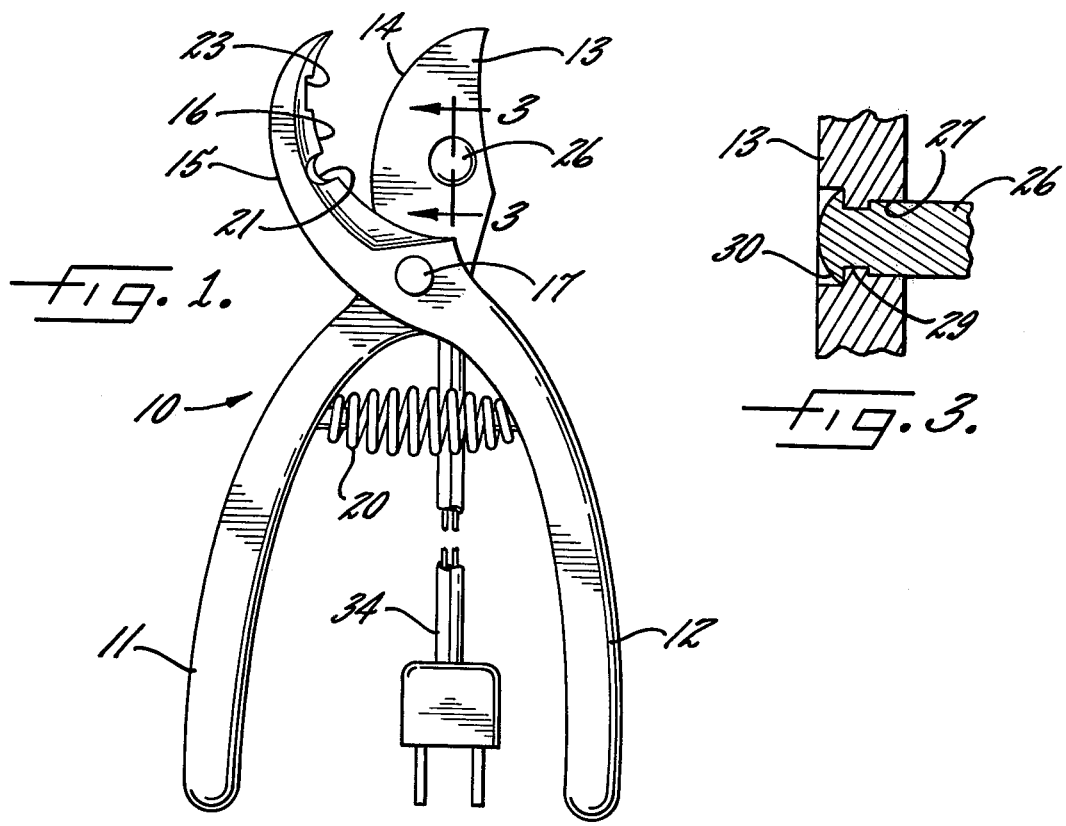
Fig. 1.
Fig. 3.
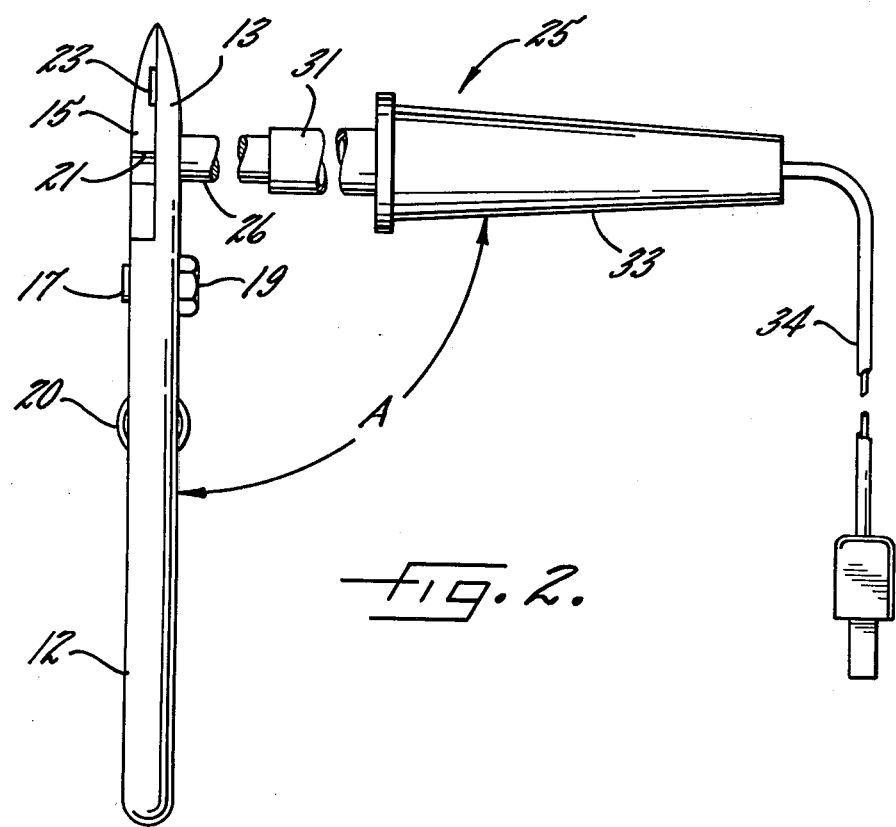
Fig. 2.

SEVERING AND CAUTERIZING INSTRUMENT FOR USE IN SEVERING TAILS AND NAVEL CORDS

CROSS-REFERENCE TO A RELATED APPLICATION

This application is a continuation of my copending application Ser. No. 565,448, filed Apr. 7, 1975 now abandoned.

BACKGROUND OF THE INVENTION

This invention relates to an instrument for severing and simultaneously cauterizing an appendage (e.g., a tail) of an animal. More particularly, the invention relates to a hand-held instrument having at least one blade for severing the appendage, the blade being heated in order to cauterize the wound and assist in blood coagulation. Instruments of this general type are disclosed in Chapman U.S. Pat. No. 1,083,386; Lagier U.S. Pat. Nos. 1,456,639 and 1,763,894 and Helbling U.S. Pat. No. 3,117,578.

SUMMARY OF THE INVENTION

The general aim of the present invention is to provide a new and improved instrument which is particularly adapted to sever and cauterize the appendages of pigs, the instrument preferably being capable of severing and cauterizing both the tail and the navel cord of a pig.

A further object is to provide a severing and cauterizing instrument having a unique blade with a notch which enables the loose skin on the tail of the pig to be pushed toward the body of the pig just before the tail is severed. After the severing operation, the loose skin rolls back over the stub of the tail and covers and protects most of the wound to promote more rapid healing and to reduce the risk of infection.

A further object is to provide a severing and cauterizing instrument in which a second notch is formed in the blade and is particularly adapted to sever the navel cord of the pig.

Another important object of the invention is to provide a severing and cauterizing instrument having a pair of scissor-type handles and having a heating element with a third handle which coacts with the scissor-type handles to form a tripod, the tripod being capable of supporting the instrument in a standing position to allow the blades to cool and to prevent the blades from becoming contaminated.

These and other objects and advantages of the invention will become more apparent from the following detailed description when taken in conjunction with the accompanying drawings.

BRIEF DESCRIPTION OF THE DRAWINGS

FIG. 1 is a front elevation of a new and improved severing and cauterizing instrument incorporating the unique features of the present invention.

FIG. 2 is a side elevation of the instrument

FIG. 3 is an enlarged fragmentary cross-section taken substantially along the line 3—3 of FIG. 1.

DETAILED DESCRIPTION OF THE PREFERRED EMBODIMENT

Figure 4:
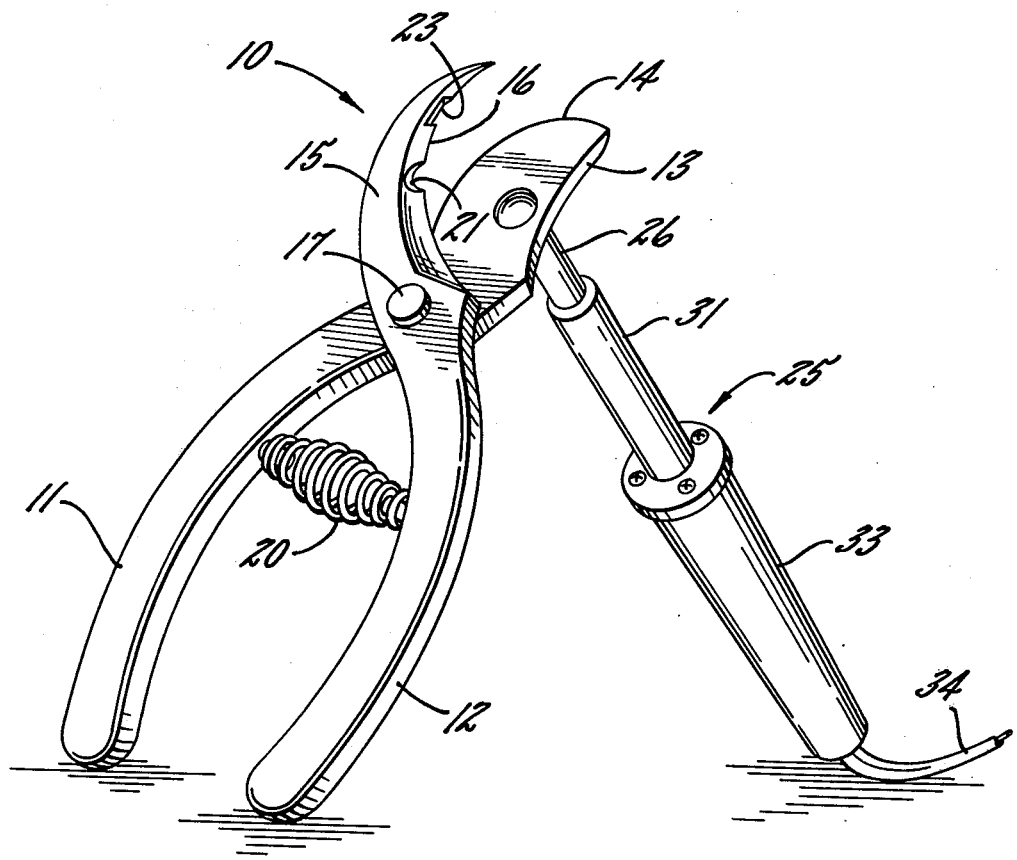
FIG. 4 is a perspective view showing the instrument being supported in a standing position by the three handles.

The present invention contemplates the provision of a new and improved instrument 10 which is especially adapted to sever and simultaneously cauterize the appendages of baby pigs. The instrument is particularly characterized by its ability to sever both the tails and navel cords of pigs, by its ability to leave a protective covering of skin around the stub of the severed tail, and by its ability to support itself in a standing position.

More particularly, the instrument 10 comprises a pair of scissor-type or plier-type handles 11 and 12. Located on one end of the handle 11 is a relatively wide blade 13 formed with a convex cutting edge 14. A narrower blade 15 is located on the corresponding end of the handle 12 and is formed with a concave edge 16. The handle 11 and the blade 13 are positioned in crossed relationship with the handle 12 and the blade 15 and are pivotally connected to the latter handle and blade by a suitable pivot which may take the form of a screw 17 and a nut 19 (FIG. 2). A coil spring 20 is compressed between the handles and urges the handles apart. When the handles are squeezed together, the blades scissor past one another to effect the severing operation.

In keeping with the invention, a substantially semi-circular notch 21 is formed in the edge 16 of the blade 15 and coacts with the cutting edge 14 of the blade 13 to sever the tail of a pig. To use the instrument to sever a tail, the tail is placed in the notch and then the blades 13 and 15 are closed sufficiently far to lock the tail in the notch but not so far as to cut the skin. Thereafter, the instrument 10 is shifted a short distance toward the body of the pig and, with the skin being locked in the notch, the skin is shifted relative to the cartilage and is pushed toward the body of the pig. The blades then are scissored to their fully closed positions to effect severing of the tail between the cutting edge 14 and the notch 21. When the blades are subsequently opened, the pushed-back portion of skin rolls outwardly over the stub and covers and protects most or all of the wound so as to keep contamination from the wound and to promote more rapid healing. Accordingly, there is less danger of the tail becoming infected than is the case when the skin is cut flush with the cartilage.

Advantageously, a second and somewhat smaller notch 23 is formed in the edge 16 of the blade 15 and coacts with the edge 14 of the blade 13 to sever the navel cord of the pig. The notch 23 is semi-rectangular in shape in that it includes a straight bottom wall and straight end walls located at the ends of the bottom wall. Thus, the semi-rectangular notch 23 allows the navel cord to flatten out and holds the cord in a closed flat position to enable even severing of the cord.

Further in carrying out the invention, an electric heating unit 25 heats the blade 13 so that the tail or navel cord will be cauterized as an incident to being severed, the heating unit coacting uniquely with the handles 11 and 12 to form a tripod for supporting the instrument 10 in a standing position. Herein, the heating unit comprises a tip or rod 26 which is telescoped into a hole 27 (FIG. 3) formed through the blade 13 and extending from one face of the blade to the other face thereof. The hole is formed with three different diameters to define an internal annular rib 29, and the rod is secured within the hole as, for example, by peening the end of the rod against the rib as indicated at 30.

Part of the rod 26 is connected to a protective heat sleeve 31 (FIG. 2) which, in turn, is connected to one end of an insulated handle 33 having a power cord 34 extending from its other end. When the power cord is connected with a suitable source of electricity, the rod 26 is heated and conducts heat to the blade 13. Accordingly, the heated blade cauterizes the stub of the appendage when the appendage is severed and thus prevents excessive bleeding and promotes more rapid healing.

As shown in FIG. 2, the rod 26 and handle 33 of the heating unit 25 are disposed at a substantial angle A relative to the handles 11 and 12. Thus, the three handles define the legs of a tripod and serve to support the instrument 10 in a standing position as shown in FIG. 4 when the instrument is not being used to perform a severing operation. In this way, the blade 13 can be heated and cooled without contacting any surface. Thus, there is no danger of the blade 13 causing a fire or burn damage and, in addition, there is no danger of the blades 13 and 15 becoming contaminated by material which otherwise would contact the blades if the instrument were laid on its side.

I claim:

1. An instrument for severing and cauterizing an appendage of a pig, said instrument comprising a first handle having a first blade with a concave edge, a second handle having a second blade with a convex edge, means pivotally connecting said first handle and said first blade with said second handle and said second blade and enabling said blades to scissor across one another when said handles are squeezed toward one another, a notch formed in the edge of one of said blades for receiving an appendage of a pig and coacting with the edge of the other blade to sever the appendage when said blades are scissored across one another, an electric heating element connected to one face of one blade and operable to heat the latter blade whereby the appendage is cauterized as an incident to being severed, and a handle connected to said heating element and disposed at an angle relative to said first and second handles whereby the three handles define a tripod for supporting said instrument in a standing position.

2. An instrument as defined in claim 1 in which said heating element comprises a rod, a hole formed through said second blade and receiving said rod, said rod being secured within said hole and having a portion extending substantially perpendicular to the face of said second blade.

3. An instrument as defined in claim 1 in which said notch is substantially semi-circular in shape and is adapted to receive the tail of a pig.

4. An instrument as defined in claim 3 further including a second notch formed in the edge of one of said blades and adapted to receive the navel cord of a pig, said second notch having a straight bottom wall and having straight end walls located at the ends of said bottom wall.

5. An instrument for severing and cauterizing the tail and navel cord of a pig, said instrument comprising a first handle having a first blade with a concave edge, a second handle having a second blade with a convex edge, means pivotally connecting said first handle and said first blade with said second handle and said blade and enabling said blades to scissor across one another when said handles are squeezed toward one another, a substantially semi-circular notch formed in the edge of said first blade for receiving the tail appendage of the pig and coacting with the cutting edge of said second blade to sever the tail appendage when said blades are scissored across one another, a substantially semi-rectangular notch formed in the edge of said first blade for receiving the navel cord appendage of the pig and coacting with the cutting edge of said second blade to sever the navel cord appendage when said blades are scissored across one another, a hole formed through said second blade and extending from one face of the second blade to the other face thereof, a rod received within said hole and having one end secured to said second blade, a third handle having one end secured to the other end of said rod and disposed at an angle relative to said first and second handles whereby the three handles define a tripod for supporting said instrument in a standing position, and an electrical cord extending from the opposite end of said third handle and operable when connected to a source of electricity to effect heating of said rod and said second blade whereby the appendage is cauterized as an incident to being severed.

* * * * *